United States Patent [19]

Chen et al.

[11] Patent Number: 4,518,792

[45] Date of Patent: May 21, 1985

[54] PROCESS FOR PREPARING N-BENZYLOXYCARBONYL-L-ASPARTIC ACID

[75] Inventors: Clay T. Chen, Edison; K. Ming Wan, East Brunswick; Mary S. Chen, Edison, all of N.J.

[73] Assignee: Hatco Chemical Corporation, Fords, N.J.

[21] Appl. No.: 526,579

[22] Filed: Aug. 26, 1983

[51] Int. Cl.³ .......................................... C07C 125/065
[52] U.S. Cl. ..................................................... 560/163
[58] Field of Search ......................................... 560/163

[56] References Cited

U.S. PATENT DOCUMENTS 3,808,190  4/1974  Dahlmans ........................... 560/163
4,293,706  10/1981  Gorman .............................. 560/163
4,345,091  8/1982  Sugiyama ........................... 560/163

OTHER PUBLICATIONS

Roberts, "An Introduction to Modern Experimental Organic Chemistry," pp. 152–158, (1969).
Mortimer, "Chemistry, A Conceptual Approach," pp. 469–473, (1967).
Greenstein, "Chemistry of the Amino Acids," vol. 2, pp. 887–901, (1961).
Dean, "Lange's Handbook of Chemistry," pp. 10–60 to 10–62, (1979), 12th Ed.
McCutcheon, "Synthetic Detergents," pp. 255, 273 & 384, (1950).
Schwartz, "Surface Active Agents," vol. 1, 3–21, 513–4, (1949).

Primary Examiner—Michael L. Shippen
Attorney, Agent, or Firm—Blum Kaplan Friedman Silberman & Beran

[57] ABSTRACT

N-Benzyloxycarbonyl-L-aspartic acid (Z-Asp) is synthesized by adding benzyl chloroformate to a solution of L-aspartic acid and sodium hydroxide at temperatures from about 5°–55° C. and over a wide pH range of about 9.2 to 13.8 in the presence of a surfactant and/or a buffer and then acidifying the reaction mixture. Carrying out the reaction in the presence of a surfactant reduces cycle time, while maintaining a high yield with low by-product content. The buffer prevents wide fluctuations in pH and minimizes localized reaction. These conditions are desirable when the reaction rate has been increased by addition of a surfactant or an increase in temperature of the reaction mixture.

22 Claims, 1 Drawing Figure

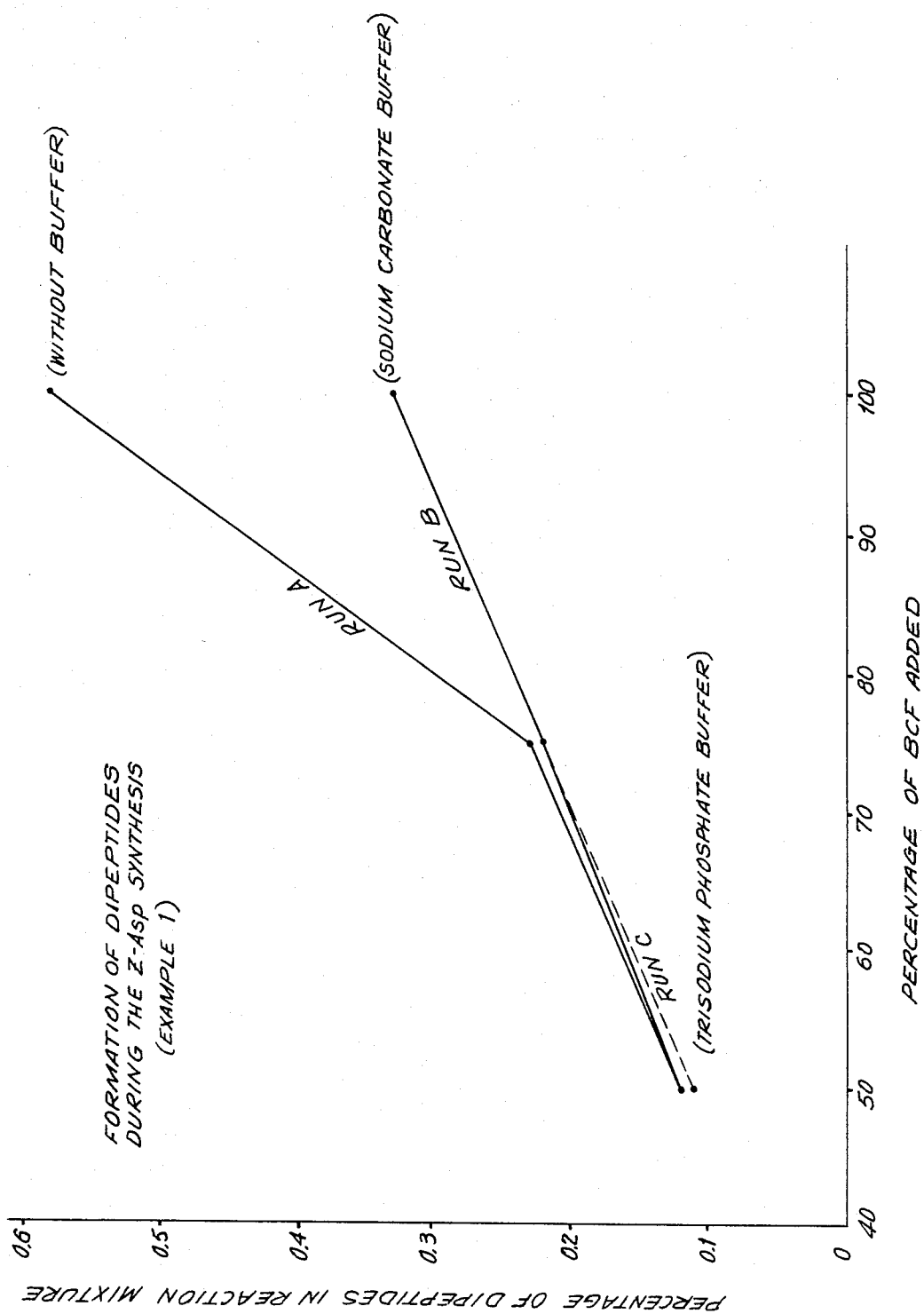

PROCESS FOR PREPARING N-BENZYLOXYCARBONYL-L-ASPARTIC ACID

BACKGROUND OF THE INVENTION

This invention relates to high purity N-benzyloxycarbonyl-L-aspartic acid (Z-Asp) suitable for the production of L-aspartyl-L-phenylalanine methyl ester (aspartame), an artificial sweetner, and more particularly to an improved method for preparing highly pure Z-Asp from L-aspartic acid (L-AA) and benzylchloroformate (BCF) in the presence of a surfactant and/or a buffer.

As aspartame is known to be about 160 times sweeter than sucrose in aqueous solution, its use as a low-calorie sweetener is highly desirable in many food applications. Aspartame is generally produced using Z-Asp as an intermediate. In view of the end use of the aspartame in food products as a substitute for sugar and other artificial sweeteners, the Z-Asp must be as pure as possible and substantially free of by-products, such as the dipeptide, N-benzyloxycarbonyl aspartyl aspartic acid (Z-Asp-Asp), benzyl chloride, benzaldehyde, dibenzyl carbonate and sodium chloride and are generally formed prior to or during the formation of the Z-Asp.

The condensation reaction of BCF with L-AA in an alkaline medium to yield Z-Asp has been well documented. Prior to 1981, the processes described in the literature did not mention the reaction conditions or suggest any additives needed to produce Z-Asp in high yield with relatively small amounts of by-products.

U.S. Pat. No. 4,293,706 which issued on Oct. 6, 1981 to Gorman, et al. teaches that Z-Asp can be prepared substantially free of Z-Asp-Asp by reacting BCF with the disodium salt of L-AA in an aqueous system within a narrow pH range of between 10.75 to 11.75. The patentees teach broadly that the reaction temperature may be maintained between 10° and 45° C., yet each of the working examples is run at room temperature which they prefer. The reactions are run without any additives which could improve the yields and purity of these products and the rate of the reactions. The patentees caution at column 2, lines 17–25 that when the reaction conditions vary, such as a pH over 12, significant hydrolysis of the benzyl chloroformate occurs and the Z-Asp product contains more than trace amounts of impurities and the yield is reduced. At column 3, lines 15–22, Gorman, et al. also note that as the temperature of the reaction increases, the amount of impurities found in the Z-Asp product tends to increase.

U.S. Pat. No. 4,354,091 issued on Aug. 17, 1982 to Sugiyama, et al. who similarly teach that Z-Asp of high purity can be prepared by reacting BCF with the dialkali metal salt of L-AA by carrying out the reaction with the pH maintained within a narrow range of 12.0 to 13.5 throughout the reaction. Sugiyama, et al. teach maintaining the temperature of the reaction between 0° and 30° C. The sole working example maintains the temperature of the reaction between 10° and 30° C. for three hours. The comparative examples show increased amount of Z-Asp-Asp when the pH falls below 12.0 together with a decrease in yield. Again, these patentees do not suggest the use of additives to promote the reaction.

While both the Gorman, et al. and Sugiyama, et al. patentees are able to provide rather strict pH and temperature reaction conditions for preparing a relatively pure Z-Asp product with relatively small amounts of Z-Asp-Asp by-product, it remains desirable to increase further the yield and purity as well as providing other improvements in the synthesis of Z-Asp. Accordingly, it is desirable to provide a method of preparing Z-Asp product in higher yields and of higher purity with lesser amounts of Z-Asp-Asp, sodium chloride and other impurities then heretofore possible.

SUMMARY OF THE INVENTION

Generally speaking, in accordance with the invention, Z-Asp is synthesized by reacting BCF with a dialkali metal salt of L-AA. The reaction is carried out in an alkaline aqueous reaction mixture within a wide range of temperatures between about 5° and 55° C. in the presence of a surfactant and/or a buffer. The surfactant increases the rate of reaction at moderate temperatures. Accordingly, it is preferable to run a reaction in the presence of buffer when using a surfactant. The buffer, even in the absence of a surfactant, tends to prevent wide fluctuation in pH at the reaction sites and results in a Z-Asp product having reduced Z-Asp-Asp. At higher temperatures, for example above room temperature, which results in faster reaction rates and in the absence of the surfactant, a buffer is used to control the pH.

Preferably, the temperature of the reaction mixture is maintained between about 20° and 50° C. with the pH within a wide range of about 9.3 to 13.8. With the temperature between about 31° and 35° C., the pH is preferably maintained between about 11.8 and 12.2.

The additives and reaction conditions yield Z-Asp in high yields equal to or better than 90% and purities equal to or greater than 99% with only small amounts of the dipeptide, Z-Asp-Asp, sodium chloride and benzyl alcohol. By controlling the concentration of the aspartic acid, the solvent, and the mode of addition of reagents, the yield of Z-Asp is increased and the formation of impurities and dipeptide may be satisfactorily controlled.

Accordingly, it is an object of the invention to provide an improved process for synthesizing Z-Asp.

It is another object of the invention to produce high purity A-Asp.

It is a further object of the invention to provide a high purity Z-Asp suitable for production of L-aspartyl-L-phenylalanine methyl ester (aspartame), an artificial sweetener.

Still another object of the invention is to provide an improved method for the preparation of Z-Asp by conducting the condensation of BCF and a dialkali metal salt of L-AA in the presence of a surfactant.

Still a further object of the invention is to provide an improved process for synthesizing Z-Asp by carrying out the condensation of L-AA and BCF in the presence of a buffer system.

Yet another object of the invention is to improve the yield of Z-Asp product by reducing the amount of water used in washing the crude product.

Yet a further object of the invention is to provide an improved method for synthesizing Z-Asp at a faster reaction rate, by decreasing the cycle time of the reaction.

It is another object of the invention to provide an improved method of synthesizing Z-Asp wherein the production of by-product Z-Asp-Asp is depressed.

It is a further object of the invention to provide an improved process for preparing high purity Z-Asp containing lesser amounts of impurities, such as benzyl alcohol, dibenzyl carbonate and polar and non-polar impurities.

Still another object of the invention is to provide a method for synthesizing Z-Asp over a broad temperature range.

Still a further object of the invention is to provide an improved process for the synthesis of Z-Asp wherein the reaction is carried out over a broad pH range and a wide temperature range which provides improved yield and purity.

Yet another object of the invention is to provide an improved process for the synthesis of Z-Asp wherein the condensation of BCF and L-AA may be carried out in the presence of an organic solvent.

Still other objects and advantages of the invention will in part be obvious and will in part be apparent from the specification.

The invention accordingly comprises the several steps and the relation of one or more of such steps with respect to each of the others, and the product possessing the features and properties which are exemplified in the following detailed disclosure, and the scope of the invention will be indicated in the claims.

BRIEF DESCRIPTION OF THE DRAWING

For a fuller understanding of the invention, reference is had to the following description taken in conjunction with the accompanying drawing, in which:

The sole FIGURE is a graph illustrating the Z-Asp-Asp concentration in the reaction mixture during synthesis of Z-Asp.

DESCRIPTION OF THE PREFERRED EMBODIMENTS

Z-Asp is the product of the condensation of BCF and a dialkali metal salt of L-AA which is then acidified to convert the Z-Asp dialkali metal salt product to the free acid. The condensation is in accordance with the following equation:

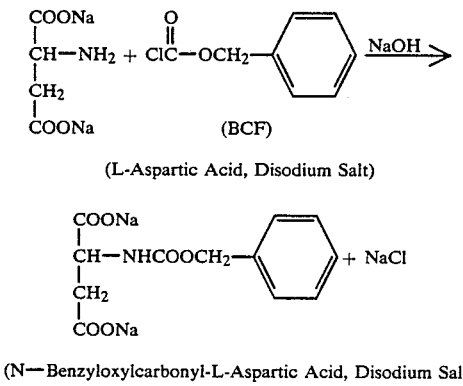

(L-Aspartic Acid, Disodium Salt)

(N—Benzyloxylcarbonyl-L-Aspartic Acid, Disodium Salt)

In accordance with the invention, the synthesis is carried out by charging L-AA and water into a reaction vessel which has been equipped with a reflux condenser, two dropping funnels, a thermometer, a pH probe and a mechanical stirrer. An aqueous alkali metal hydroxide, such as sodium or potassium hydroxide is added under stirring until all the amino acid is dissolved. A surfactant and/or buffer are then added.

Benzyl chloroformate and additional dilute caustic are added simultaneously at the desired pH between about 9.2 and 13.8 while maintaining the temperature between about 5° and 55° C. The temperature of the reaction mixture is preferably maintained at between about 20° to 45° C. with the pH between about 11.0 to 12.5. Most preferably the temperature is maintained between about 31° to 35° C. and the pH between about 11.8 to 12.2. A slight excess of BCF may be added. The reaction is considered complete when there is little or no unreacted L-AA detected in the system. The presence of unreacted L-AA in the reaction mixture is monitored by the Ninhydrin method. The reaction mixture is then cooled. After adjusting the aqueous system to a pH of between about 6 and 7 with hydrochloric acid, the organic layer is removed.

The aqueous layer is then acidified with concentrated HCl. The reaction mixture is maintained at 20° to 45° C. until the growth of crystals is completed, and it is then gradually cooled to 5° to 10° for several hours. Crystals of Z-Asp are collected by centrifugation, washed with ice water and dried.

The reaction of the L-AA and BCF may be carried out in the presence of an organic solvent which can have a density higher or lower than water, such as 1,1,1-trichloroethane, methylene chloride, toluene, chlorobenzene and the like. The organic solvent can be added to the reaction medium prior to the addition of BCF or admixed with the BCF. The organic solvents suppress the hydrolysis of BCF and also help to remove the impurities, such as benzyl alcohol, benzyl chloride, dibenzyl carbonate and the like which can be formed during or prior to the reaction. The ratio of organic solvent to BCF is not critical. Generally, between about 0.02 to 2.0 parts by volume of solvent to 1.0 part of BCF is used.

In accordance with a first embodiment of the invention, the reaction is carried out in the presence of a buffer. Suitable buffers include sodium carbonate, sodium bicarbonate, trisodium phosphate, disodium phosphate and sodium hexametaphosphate. The buffer tends to prevent wide fluctuations in pH and minimize localized reactions within the reaction vessel. The amount of buffer may vary between about 4% and 40% by weight of the L-AA depending on the nature of the buffer used. The buffer can be added prior to the addition of BCF, or during the course of the reaction. The addition of buffer minimizes pH fluctuations and suppresses the formation of Z-Asp-Asp. This is important when the rate of the reaction is increased by running the reaction at elevated temperatures or by addition of a surfactant as will be discussed in more detail below.

The significance of the presence of a buffer is demonstrated by the results of Runs A, B and C of Example 1 as shown in the Figure.

EXAMPLE 1

Each run was carried out in a 30 gallon glass lined reactor equipped with a mechanical stirrer, circulation pump, pH probe and a temperature measuring device. A charge of 15.0 liters of water, 5.0 Kg of L-AA, about 11.1 Kg of 25% NaOH solution and the $Na_2CO_3$ or $Na_3PO_4.12H_2O$ buffer was placed in the reactor as indicated in Table I. After adjusting the reaction mixture to pH 10.5 to 10.7, it was heated to 45°–46° C. as indicated in Table I. The benzyl chloroformate was added at a rate of about 4.5 Kg/hr. to the reaction mixture together with enough dilute NaOH solution to maintain the pH range. The temperatures were maintained between 45° and 48° C. throughout the reaction as indicated.

During each run a small sample was taken periodically and the dipeptide content of the reaction mixture was determined and it is shown in the FIGURE.

After cooling the reaction mixture to room temperature, the oragnic layer was separated. The aqueous solution was acidified with concentrated HCl and the Z-Asp was crystallized, initially at 30°–35° C., then at 10° C. for 2 hours. The crude product was centrifuged and washed with an amount of ice water equal to the weight of the product and dried. The product from Run A which was prepared in the absence of a buffer, was obtained in 88% yield and 99.5% purity. The products from Runs B and C were obtained in 92.7% and 93.6% yields and purities of 100.1% and 99.8%. In particular the amount of dipeptide present in Run A is about 75% greater than in Runs B and C and the benzyl alcohol content is significantly greater in Run A than in B and C. The results are summarized in Table 1.

The mode of action of the buffers is not clear, but it is believed that the presence of a buffer minimizes wide pH fluctuations during the course of the reaction. As localized acidity is decreased, the change of dipeptide formation is also decreased. When carrying out the synthesis of Z-Asp in the presence of a buffer, the buffer is added to the reaction mixture after the L-AA is dissolved.

TABLE I

| | Example 1 | | |
|---|---|---|---|
| | RUN A | RUN B | RUN C |
| REACTANTS | | | |
| L-AA g (mole) | 5000 (37.57) | 5000 (37.57) | 5000 (37.57) |
| BCF 95% g, (mole) | 7050 (41.28) | 7070 (41.44) | 7210 (42.26) |
| $Na_2CO_3$ g | — | 1000 | — |
| $Na_3PO_4.12H_2O$ g | — | — | 1000 |
| REACTION CONDITIONS | | | |
| Temp., °C. | | | |
| Initial | 46.2 | 46.4 | 47.6 |
| Reaction | 46.0–47.9 | 46.0–47.6 | 45.0–48.0 |
| pH Range | 10.7–11.0 | 10.7–11.0 | 10.5–11.0 |
| PRODUCT ANALYSIS | | | |
| Yield g, (%) | 8800 (88.0) | 9305 (92.7) | 9396 (93.6) |
| Assay % | 99.5 | 100.1 | 99.8 |
| *Dipeptides % | 0.25 | 0.12 | 0.15 |
| *BZOH % | 0.33 | 0.01 | 0.01 |

*Analyzed by HPLC in area %

In accordance with a second embodiment of the invention, the condensation reaction of BCF and L-AA is carried out in the presence of a surfactant. The presence of a surfactant tends to minimize localized reactions, and it helps to promote dispersion. Under these conditions the reactions proceed smoothly and at a faster reaction rate which decreases the cycle time of the reaction.

The structure and type of surfactant is also not critical. Quaternary ammonium chlorides, sulfonates, polyethoxylated quaternary ammonium salts and amine oxides may be used. Examples of quaternary ammonium salts include trimethylhexadecylammonium chloride, dimethyldioctadecylammonium chloride, trimethyltallowammonium chloride and the like. Cationic, anionic and amphoteric surfactants can be used. The concentration of surfactant is not critical and can range from a minimum effective amount of about 0.01% to 5.00% by weight of the L-AA used.

In Examples 2 and 3 comparative runs were performed to show the increase in reaction rate due to the presence of a surfactant. In both cases, the reactions were run using the same equipment as used in Example 1.

EXAMPLE 2

In a 30-gallon glass-lined reactor equipped with a mechanical stirrer, circulation pump, pH probe and a temperature measuring device was placed 24.0 liters of water, 8.0 Kg of L-AA, about 17.8 Kg of 25% NaOH solution, 8 g of Arquad 16-50 (a 50% solution of trimethylhexadecylammonium chloride from Armak Co., Chicago, Ill.) as a surfactant and 1.6 Kg of $Na_3PO_4.12H_2O$ as a buffer. After adjusting the reaction mixture to pH 11.8 to 11.9, it was heated to 32°–34° C. Benzyl chloroformate (about 11.3 Kg, 95% purity) mixed with 4 Kg of 1,1,1 trichloroethane was added at a rate of about 6 Kg/hr. to the reaction mixture together with enough dilute NaOH solution to maintain the pH within range. The temperature was maintained between 32°–34° C. throughout the reaction. The reaction was completed after 200 minutes from the start of addition of BCF. At that time little or no unreacted L-AA was detected.

After cooling the reaction mixture to room temperature, the organic layer was separated. The aqueous solution was acidified with concentrated HCl and the Z-Asp was crystallized, initially at 30°–35° C., then at 10° C. for 2 hours. The crude product was centrifuged, washed with about 10 liters of ice water and dried. The purity of the final product was more than 99.9% and it contained equal to or less than 0.8% dipeptide, 0.1% benzyl alcohol, 0.2% unreacted L-AA and 0.16% sodium chloride. The starting materials and results are summarized in Table II.

EXAMPLE 3

In order to compare the effect of the surfactant on the reaction rate, a duplicate run was carried out using the same quantities of reactants and equipment as in Example 2. The reaction conditions were identical to Example 2, except that the temperature was raised somewhat to 35°–38° C. Notwithstanding the increased temperature, the reaction took 360 minutes to complete. The crude product was washed with 15 liters of ice water. The quality of the product was about the same as that of Example 1. The starting materials and results for both Examples 2 and 3 are summarized in Table II.

TABLE II

| | EXAMPLE 2 | EXAMPLE 3 |
|---|---|---|
| REACTANTS | | |
| L-AA g (mole) | 8,000 (60.1) | 8,000 (60.1) |
| BCF 95% g, (mole) | 11,300 (66.2) | 11,300 (66.2) |
| Arquad 16-50, g | 8 | — |
| Solvent g | TCE 4000 | TCE 4000 |
| $Na_2CO_3$ g | — | — |
| $Na_3PO_4.12H_2O$, g | 1,600 | 1,600 |
| REACTION CONDITIONS | | |
| Temp., °C. | | |
| Initial | 31.9 | 35.1 |
| Reaction | 32–34 | 35–38 |
| pH Range | 11.8–11.9 | 11.8–11.9 |
| Reaction Time (min.) | 200 | 360 |
| PRODUCT ANALYSIS | | |
| Yield g, (%) | 15,208 (94.7) | 15,143 (94.3) |
| Assay % | 99.9 | 100.1 |
| *Dipeptides % | 0.08 | 0.08 |
| L-AA % | 0.2 | 0.2 |
| NaCl % | 0.16 | 0.14 |
| *BZOH % | 0.1 | 0.1 |

*Analyzed by HPLC in area %

The surfactant serves several purposes. In a heterogeneous reaction like the present process, the BCF alone or combined with an organic solvent is immiscible with water. When it is added to an aqueous solution containing the dialkali metal salt of the L-AA, the reaction takes place mostly at the interface between the two phases. The localized reaction may generate excess HCl at the reaction sites and the pH may be lower than in the reaction mixture as a whole. The localized acidity may lead to the formation of Z-Asp-Asp. The surfactant helps the two phases mix more uniformly, and thus the reaction takes place throughout the reaction medium. In so doing, any localized reactions are not only greatly minimized, but the reaction rate is much faster and the reaction time is reduced substantially as shown in Example 2 in Table II.

Another advantage attained by use of the surfactant is a reduction in the amount of water needed for washing the crude product. In runs without surfactant, the amount of ice water required is equal to about the weight of the product so that the dry products will contain less than 0.2% of sodium chloride. With the aid of the surfactant, the amount of ice water wash can be reduced. In Example 2 where no surfactant was used the dry product weighed about 15143 g and it had been washed with 15 liters of ice water. The sodium content in the dry product is 0.14%. In Examples 4, 5, 6 and 7 where surfactants were used the weight of the ice water wash was reduced to about 40% of the weight of the products, even so each product contained 0.1% or less sodium chloride. The results are summarized in Tables II and III.

Still another advantage of the use of surfactant is the ability to remove other impurities, such as benzyl alcohol from the product during washing. In runs without a surfactant, the crystals of Z-Asp generally contain trace amounts of benzyl alcohol as analyzed by high pressure liquid chromatography. In cases where a surfactant is used, the presence of benzyl alcohol is negligible.

As described above, a surfactant serves several purposes, therefore, it can be added at different stages of the reaction depending on the desired result. The surfactant can be added prior to the addition of the BCF to facilitate the reaction and removal of impurities. Or, if removing impurities are the prime objectives, it can be added after the reaction is completed or during the washing of the crude product.

It is well known that reaction rates are faster at higher temperatures, However, BCF tends to hydrolyze more rapidly at higher temperatures which lower yields and increase impurity. At lower temperatures, the reaction rates are slower and excess BCF accumulates in the reaction mixture which also favor hydrolysis. With the addition of a surfactant, the reaction can be run at a moderate temperature, yet at a reaction rate almost as fast as a high temperature process without accompanying significant BCF hydrolysis. In view of this increase in the reaction rate it is preferable to include a buffer in the reaction mixture when the reaction is run with a surfactant.

The following Examples 4 to 8 illustrate synthesis of Z-Asp in accordance with the preferred embodiments of the invention wherein the condensation of BCF and L-AA is carried out in the presence of both a buffer and a surfactant or at high temperature in the presence of a buffer. They are presented by way of illustrations only and are not intended in a limiting sense. The equipment used and the procedure followed are set forth in the description of Example 4.

EXAMPLE 4

In a 2 liter multi-necked flask equipped with a reflux condenser, two dropping funnels, a thermometer, a pH probe and mechanical stirrer was placed 133.1 grams (1.00 mole) of L-AA and 400 ml water. A 25% NaOH solution was added with stirring until the L-AA was fully dissolved and 0.15 gram Arquad 16-50 as a surfactant was added. About 185 grams (1.03 moles) of 95% pure BCF mixed with 8 grams of chlorobenzene solvent was added to the reaction mixture with sufficient dilute NaOH solution with stirring to maintain the pH of the reaction mixture at a pH between 13.0-13.3. The temperature was initially 10° C. and it was maintained between about 8°-10° C. during the addition of the BCF. The presence of unreacted L-AA in the reaction mixture was monitored by the Ninhydrin method. The reaction was completed after an additional time of 112 minutes and little or no unreacted L-AA was detected in the reaction mixture. More TCE was added to the reaction mixture to facilitate phase separation.

After separating the organic layer from the reaction mixture the aqueous solution was acidified with concentrated HCl and the Z-Asp was crystallized, initially at 30°-35° C., then at 10° C. for 2 hours. The crude product was centrifuged and washed with about 40% of its weight of ice water and dried. The purity of the final product was about 100% and it contained 0.03% dipeptide, negligible benzyl alcohol, less than 0.2% unreacted L-AA and 0.1% sodium chloride. The reactants, reaction conditions and product analyses are set forth in Table III.

The reaction conditions (temperature and pH) approximate the preferred conditions taught in U.S. Pat. No. 4,345,091 (Sugiyama, et al.). According to the patent example, the reaction time for 0.6 mole L-AA at 10°-30° C., pH 12.5-13.5 was 180 minutes. In contrast, this Example 4 including a surfactant in accordance with the invention at below 10° C. took only 112 minutes for 1.0 mole of L-AA. The other results also compare favorably as follows:

|  | U.S. Pat. No. 4,345,095 | Example 4 |
| --- | --- | --- |
| BCF, excess % | 10 | 3 |
| Yield, % | 36.2 | 41.2 |
| L-AA | 1.0 | 0.2 |

EXAMPLE 5

In order to show the effect of surfactant on the reaction rate at an extremely high pH, a duplicate run to Example 4 was carried out using the same quantities of reagents and equipment. The reaction conditions were identical to Example 4, except the temperature was maintained at 4°-5° C. with the pH at 13.8-14.1 (mainly 14.0). The yield of the product was reduced and the L-AA and benzyl alcohol in the product was about the same as in Example 4. The results are summarized in Table III.

EXAMPLES 6, 7 AND 8

Examples 6 and 7 follow the procedure of Example 4. Example 6 was run at a moderate temperature of 24°-30° C. and a pH of 11.7-12.0. Example 7 was run at a higher temperature of 42°-44° C. and a somewhat lower pH of 10.5–11.3. Example 8 illustrates a high temperature reaction at 46°–48° C. in the presence of a buffer, but not in the presence of an organic solvent or surfactant. The reactants, reaction conditions and product analyses are set forth in Table III.

TABLE III

| REACTANTS | EXAMPLE 4 | EXAMPLE 5 | EXAMPLE 6 | EXAMPLE 7 | EXAMPLE 8 |
|---|---|---|---|---|---|
| L-AA g. (mole) | 133.1 (1.00) | 133.1 (1.00) | 133.1 (1.00) | 133.1 (1.00) | 39.9 (0.30) |
| BCF 95%, g, (mole) | 185 (1.03) | 188 (1.05) | 184 (1.03) | 182 (1.01) | 54 (0.30) |
| Arquad 16-50, g | 0.15 | 0.15 | 0.15 | 0.15 | — |
| Solvent, g | chlorobenzene, 8 | chlorobenzene, 9 | TCE, 80 | chlorobenzene, 10 | — |
| $Na_2CO_3$ g | — | — | — | 10 | — |
| $Na_3PO_4.12H_2O$ g | — | — | 26 | — | 8 |
| REACTION CONDITIONS | | | | | |
| Temp., °C. - Initial | 10 | 5 | 24 | 34 | 40 |
| - Reaction | 8–10 | 4–5 | 24–30 | 42–44 | 46–48 |
| pH Range | 13.0–13.3 | 13.8–14.1 | 11.7–12.0 | 10.5–11.3 | 10.50–11.10 |
| PRODUCT ANALYSIS | | | | | |
| Yield g, (%) | 243.5 (91.2) | 2220 (83.2) | 245.7 (92.0) | 222.5 (94.6) | 76.5 (95.5) |
| *Assay % | 100.0 | 99.4 | 99.8 | 100.0 | 99.80 |
| **Dipeptides % | 0.03 | 0.02 | 0.06 | 0.10 | 0.10 |
| L-AA % | 0.2 | 0.2 | 0.2 | 0.2 | trace |
| *NaCl % | 0.1 | 0.1 | 0.1 | 0.1 | 0.2 |
| **BZOH % | negligible | negligible | negligible | negligible | negligible |

*Analyzed by titiation
**Analyzed by high pressure liquid chromatography in area %

Z-Asp is synthesized in accordance with the invention by condensing BCF with a dialkali metal salt of L-AA at temperatures between 5°–55° C. and at a broad pH range of between 9.2 to 13.8 in the presence of a surfactant or a buffer, or both a surfactant and a buffer. In the most preferred embodiment of the invention, the temperature of the reaction mixture is maintained between about 31°–35° C. with the pH of the reaction mixture maintained between about 11.8–12.2 in the presence of both a buffer and a surfactant. By carrying out the reaction under these conditions in accordance with the invention, higher quality Z-Asp in higher yield can be obtained with the cycle time of the reaction substantially reduced.

It will thus be seen that the objects set forth above, among those made apparent from the preceding description, are efficiently attained and, since certain changes may be made in carrying out the above process and in the described product, set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

What is claimed is:

1. A method of synthesizing N-benzyloxycarbonyl-L-aspartic acid by condensing benzyl chloroformate and a dialkali metal salt of L-aspartic acid in an alkaline aqueous solution, comprising added benzyl chloroformate and an alkalai metal hydroxide solution to an alkaline aqueous mixture containing L-aspartic acid maintained at a pH of at least about 9.2 in the presence of at least one of a buffer and a surfactant and then acidifying the reaction mixture upon completion of the reaction, whereby the N-benzyloxycarbonyl-L-aspartic product is of higher purity than product obtained at the same reaction conditions in the absence of a buffer and/or a surfactant.

2. The method of claim 1, wherein the condensation reaction is carried out in the presence of a buffer.

3. The method of claim 2, wherein the temperature of the reaction mixture is maintained between about 31°–55° C.

4. The method of claim 3, wherein the pH of the reaction mixture is maintained between about 11.0–12.5.

5. The method of claim 2, wherein the pH of the reaction mixture is maintained between about 11.8–12.2 and the temperature is maintained between about 31°–35° C.

6. The method of claim 2, wherein the buffer is present in amounts between about 4 to 40 percent by weight based on the weight of the L-aspartic acid.

7. The method of claim 2, wherein the buffer is selected from the group consisting of sodium carbonate, sodium bicarbonate, trisodium phosphate, disodium hydrogen phosphate and sodium hexametaphosphate.

8. The method of claim 1, wherein the condensation reaction is carried out in the presence of a surfactant.

9. The method of claim 8, wherein the temperature of the reaction mixture is maintained between about 31°–35° C.

10. The method of claim 9, wherein the pH of the reaction mixture is maintained between about 11.0–12.5.

11. The method of claim 8, wherein the pH of the reaction mixture is maintained between about 11.8–12.2 and the temperature is maintained between about 31°–35° C.

12. The method of claim 8, wherein the surfactant is present in amounts between about 0.01 to 5.00 percent by weight based on the weight of the L-aspartic acid.

13. The method of claim 8, wherein the surfactant is selected from the group consisting of quaternary ammonium chlorides sulfonates, polyethoxylated quaternary ammonium salts and amine oxides.

14. The method of claim 1, wherein the condensation reaction is carried out in the presence of both a buffer and a surfactant.

15. The method of claim 14, wherein the pH of the reaction mixture is maintained between about 11.8–12.2 and the temperature is maintained between about 31°–35° C.

16. The method of claim 1, further including the step of mixing the benzyl chloroformate with an organic solvent prior to adding the benzyl chloroformate to the reaction mixture containing L-aspartic acid.

17. The method of claim 1, wherein the alkali metal hydroxide is sodium hydroxide.

18. The method of claim 1, wherein the reaction mixture is acidified with hydrochloric acid.

19. A method of synthesizing N-benzyloxycarbonyl-L-aspartic acid by condensing benzyl chloroformate and a dialkali metal salt of L-aspartic acid in an alkaline aqueous solution, comprising adding benzyl chloroformate and an alkali metal hydroxide solution to an alkaline aqueous mixture containing L-aspartic acid in the presence of a buffer and a surfactant while maintaining the pH of the reaction mixture between about 11.8–12.2 and the temperature between about 31°–35° C. and acidifying the reaction mixture upon completion of the reaction, whereby the N-benzyloxycarbonyl-L-aspartic product is of higher purity than the product obtained at the same reaction conditions in the absence of a buffer and/or surfactant.

20. The method of claim 19, further including the step of mixing the benzyl chloroformate with an organic solvent prior to adding the benzyl chloroformate to the reaction mixture containing L-aspartic acid.

21. The method of claim 19, wherein the alkali metal hydroxide is sodium hydroxide.

22. The method of claim 19, wherein the reaction mixture is acidified with hydrochloric acid.

* * * * *